(12) United States Patent
Yau et al.

(10) Patent No.: US 8,077,942 B2
(45) Date of Patent: Dec. 13, 2011

(54) METHOD FOR DESIGNING AN ABUTMENT

(75) Inventors: Hong-Tzong Yau, Chen Cuo Liao (TW);
Chuan-Chu Kuo, Gongguan (TW);
Jiun-Ren Chen, Sijing (TW); Chine-An Chen, Lujhu Township, Kaohsiung County (TW)

(73) Assignee: Pou Yu Biotechnology Co., Ltd., Changhua County (TW)

( * ) Notice: Subject to any disclaimer, the term of this patent is extended or adjusted under 35 U.S.C. 154(b) by 922 days.

(21) Appl. No.: 12/038,611

(22) Filed: Feb. 27, 2008

(65) Prior Publication Data

US 2009/0104583 A1    Apr. 23, 2009

(30) Foreign Application Priority Data

Oct. 22, 2007   (TW) .............................. 96139461 A (51) Int. Cl.
*G06K 9/00* (2006.01)

(52) U.S. Cl. ........................................ 382/128; 382/154
(58) Field of Classification Search ................ 433/213, 433/214, 24, 172–176, 72, 75; 382/154, 382/128; 250/234; 356/601; 700/98, 87, 700/118; 264/17–18
See application file for complete search history.

(56) References Cited

U.S. PATENT DOCUMENTS 6,788,986 B1 * 9/2004 Traber et al. .................... 700/98

* cited by examiner

*Primary Examiner* — Sunil K Singh (57) ABSTRACT

A method for designing an abutment tooth which mainly comprises the steps of: setting a reference abutment device with a feature on an analog of a mouth model; positioning a digital abutment with the same configuration as the reference abutment device on the analog to obtain the configuration data of the positioning of the digital abutment on the analog; optimally adjusting the digital abutment by using as a reference the configuration digital data without affecting the configuration of the digital abutment and the analog, thus finishing the design of the abutment.

4 Claims, 13 Drawing Sheets

METHOD FOR DESIGNING AN ABUTMENT

BACKGROUND OF THE INVENTION

1. Field of the Invention

The present invention relates to a dental implant abutment, and more particularly to a method for designing an abutment.

2. Description of the Prior Art

Conventionally, when an abutment is fabricated, in order to fix the artificial tooth at the optimal position, a design software package is utilized to design and modify the configuration of the abutment. To design and modify the abutment, a model of the inside of the patient's mouth needs to be reproduced first. Then the mouth model is scanned by a scanner. Finally, the scanned abutment is designed and modified through the use of a design software package. However, the conventional design and modification of the abutment still has the following disadvantages:

Since the interface of the analog in the mouth model is not obvious, only the digital data of the mouth model can be obtained after scanning, and an accurate digital data of the analog interface cannot be obtained. Furthermore, since the connection of the analog and the abutment has a specific configuration, that is to say, they are connected at a specific angle, and since it is not possible to obtain digital data of the analog interface, if the configuration of the abutment is adjusted, although artificial tooth fabrication can obtain the best occlusion relation and the best tooth arrangement data using software, deviation in configuration between the abutment and the analog can result.

Hence, if the conventional technique does not perform adjustments based on the positioning configuration of the interfaces of the abutment and the analog, once the adjusted abutment is fabricated as a finished product, and the finished abutment product is installed at the implant site, the deviation caused by the adjustment of the abutment will result in the loss of occlusion data, reducing the occlusion functionality of the artificial tooth, and in the loss of tooth arrangement data, spoiling the esthetics of the artificial tooth after dental implantation.

The present invention mitigates and/or obviates the above mentioned disadvantages.

SUMMARY OF THE INVENTION

The primary objective of the present invention is to provide a method for designing an abutment. The method allows the adjustment of the abutment according to requirements without affecting the configuration relation with respect to the analog so as to obtain definite tooth arrangement data for artificial tooth fabrication, improving the esthetics of the implanted artificial tooth.

A second objective of the present invention is to provide a method for designing an abutment. The method allows for the adjustment of the abutment according to requirements without affecting the configuration relation with respect to the analog so as to obtain definite occlusion relation data for artificial tooth fabrication, improving the functionality of the artificial tooth.

In order to achieve the above objectives, a method for designing an abutment in accordance with the present invention comprises the steps of acquiring a mouth model, which consists of reproducing the inside of a patient's oral cavity to form a mouth model, the mouth model having an analog at an implant site of the mouth model, where the analog includes an interface; setting a reference abutment device, which consists of fetching a reference abutment device with an interface, where the reference abutment device includes at least one feature on the outer surface thereof, and where the interface of the reference abutment device is positioned on the interface of the analog such that the feature on the reference abutment device is not blocked by adjacent teeth; scanning, which consists of scanning the mouth model to obtain a digital mouth model, a digital reference abutment device model, and a digital data of the feature on the reference abutment device; positioning, which consists of taking a digital positioning abutment device, a positioning element within the digital positioning abutment device, and a digital abutment, where the digital positioning abutment device includes at least one feature on its outer surface, and where the digital positioning abutment device is superimposed on the digital reference abutment device to substitute for the digital reference abutment device using the feature of the digital positioning abutment device as reference and where the digital positioning abutment device substitutes for the digital reference abutment device, so as to obtain the digital configuration data of the positioning of the digital positioning abutment device on the interface of the analog, the digital abutment being superimposed on the digital reference abutment device; adjusting, which consists of the digital abutment being optimally adjusted by using as a reference the digital configuration data of the digital positioning abutment device and the analog, thus finishing the abutment design.

DETAILED DESCRIPTION OF THE PREFERRED EMBODIMENTS

The present invention will be clearer from the following description when viewed together with the accompanying drawings, which show, for the purpose of illustrations only, the preferred embodiment in accordance with the present invention.

Figure 1:
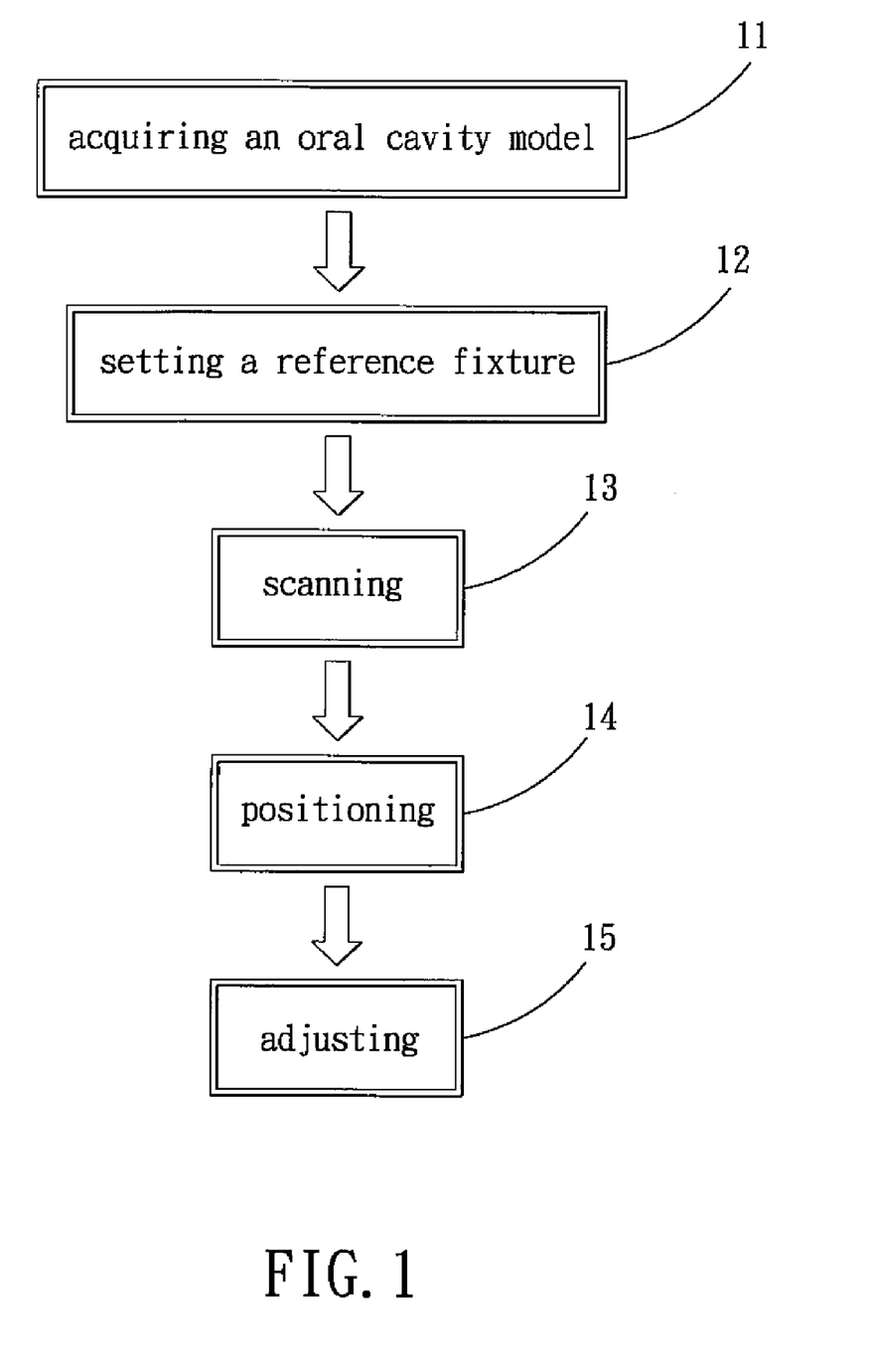
FIG. 1 is a flowchart of a method for designing an abutment in accordance with the present invention.

Please refer to FIG. 1 first, which shows a method for designing an abutment in accordance with the present invention which comprises the steps of: acquiring a mouth model 11; setting a reference abutment device 12; scanning 13; positioning 14; and adjusting 15.

Figure 2:
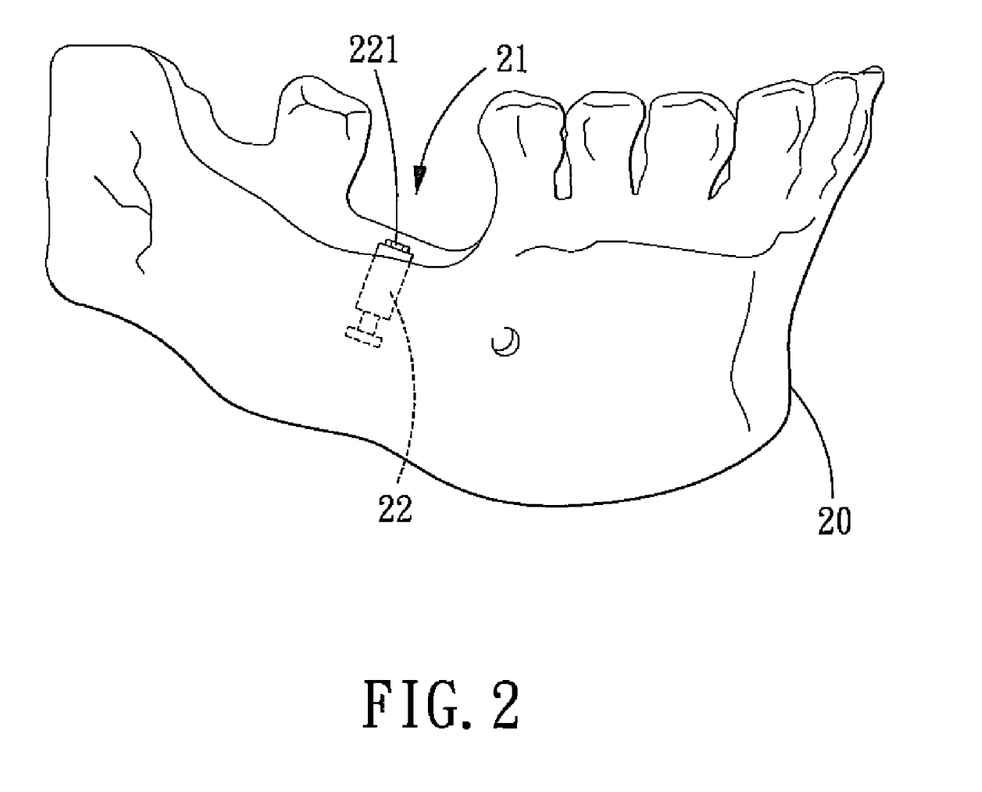
FIG. 2 is a schematic view of the step of acquiring a mouth model in accordance with the present invention, illustrating that the mouth model includes an analog.
Figure 3A:
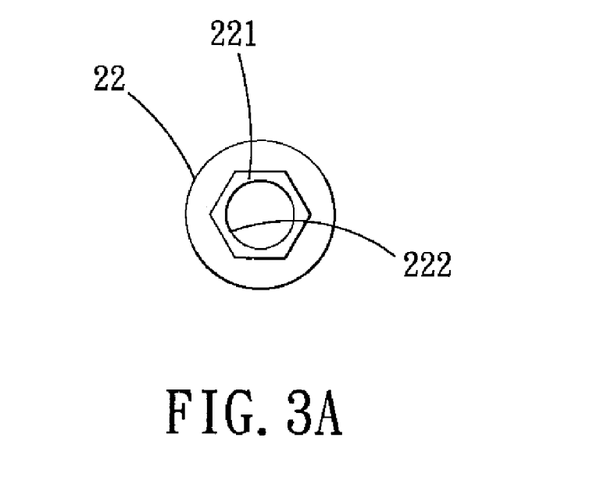
FIG. 3A is a top view of the analog with a hexagonal interface in accordance with the present invention.
Figure 3B:
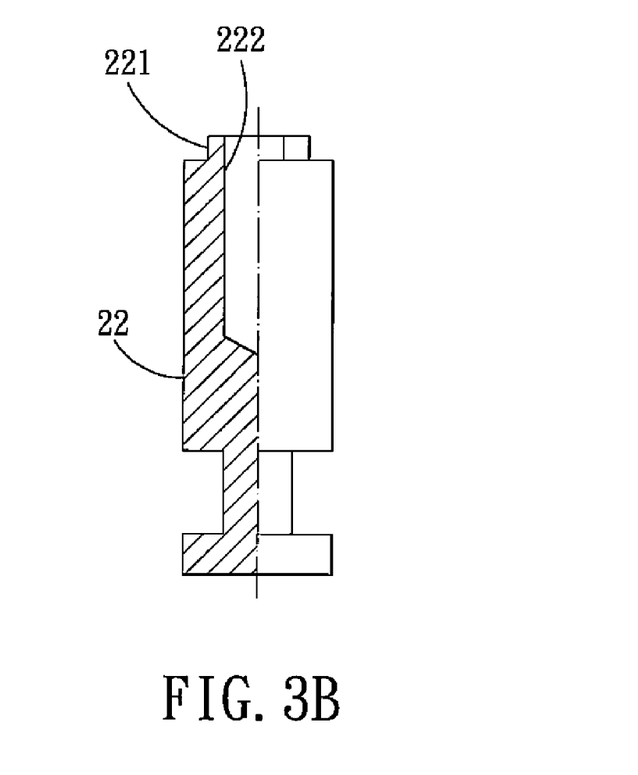
FIG. 3B is a partial cross sectional view of the analog in accordance with the present invention, illustrating the interior of the analog.

As shown in FIGS. 2-3B, in the step of acquiring the mouth model 11, which consists of reproducing the inside of the patient's oral cavity to create a mouth model 20, at the dental implant site of the mouth model 20 is an analog 22 having an exposed interface 221. In the present embodiment, the interface 221 of the analog 22 is, for example, in the shape of a hexagon, and the interface 221 can also be in various conventional shapes, such as a triangle, petal shape, and so on.

Figure 4:
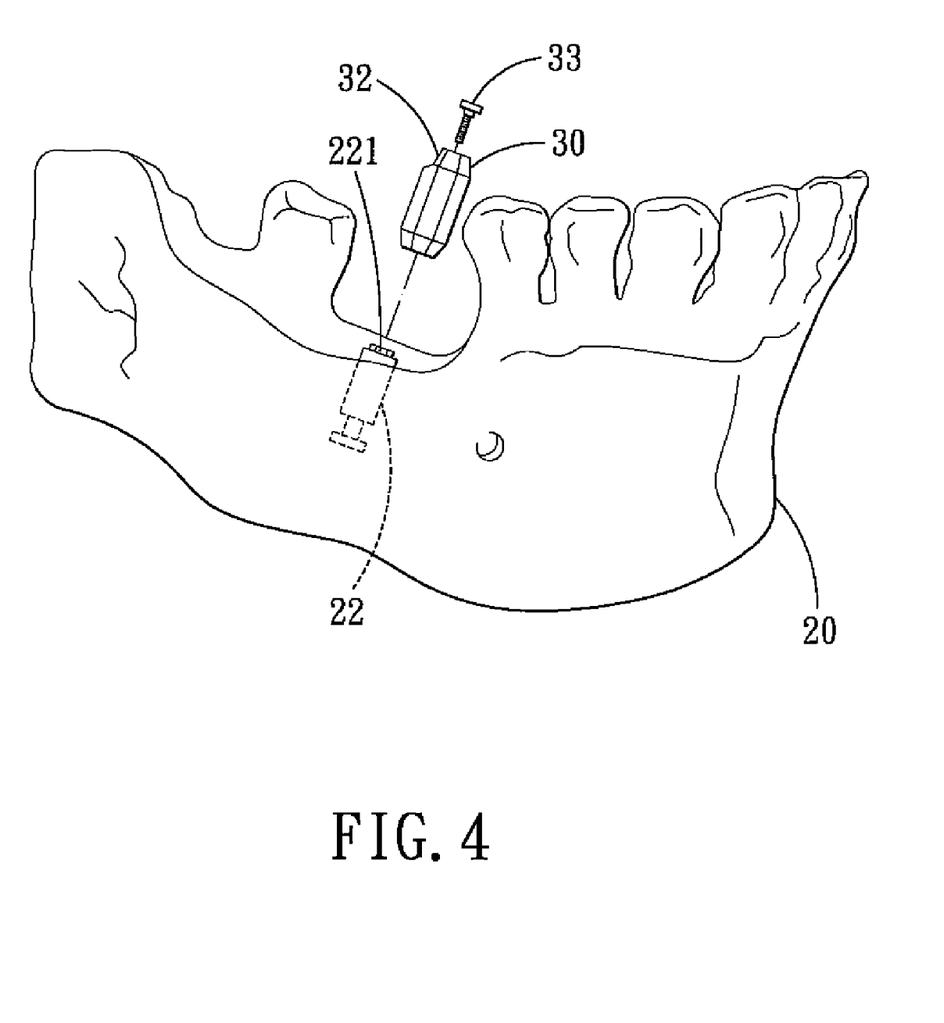
FIG. 4 is an exploded view illustrating a reference abutment device in accordance with the present invention.
Figure 5A:
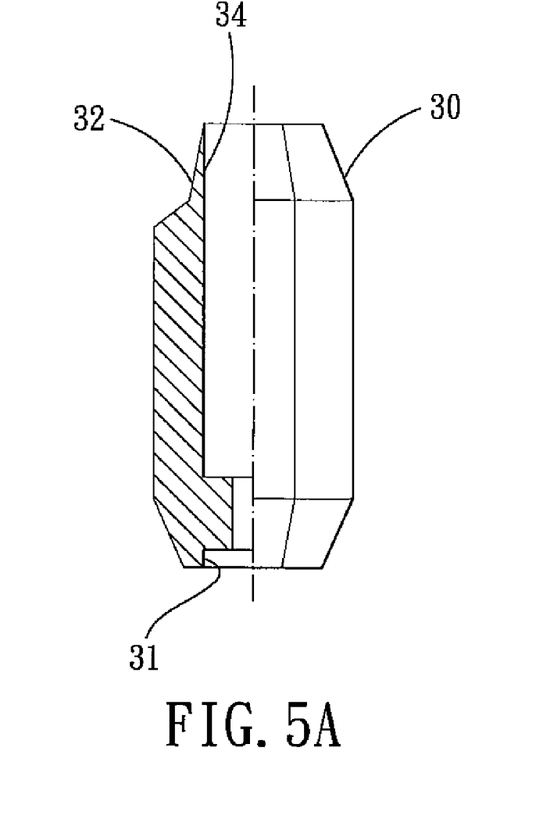
FIG. 5A is a partial cross sectional view of the reference abutment device in accordance with the present invention, illustrating the internal configuration of the implant.
Figure 5B:
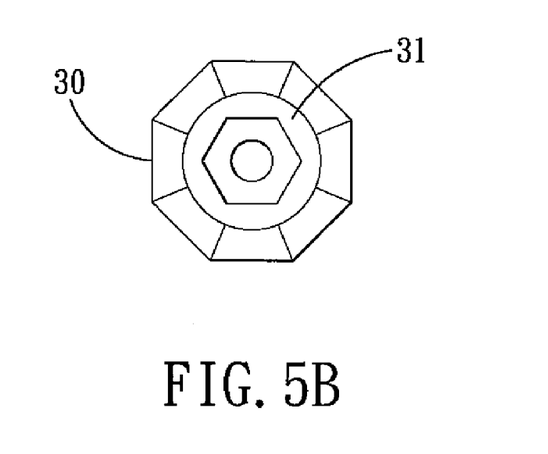
FIG. 5B is a bottom view of the reference abutment device in accordance with the present invention, illustrating that the interface of the reference abutment device is hexagonal.
Figure 6:
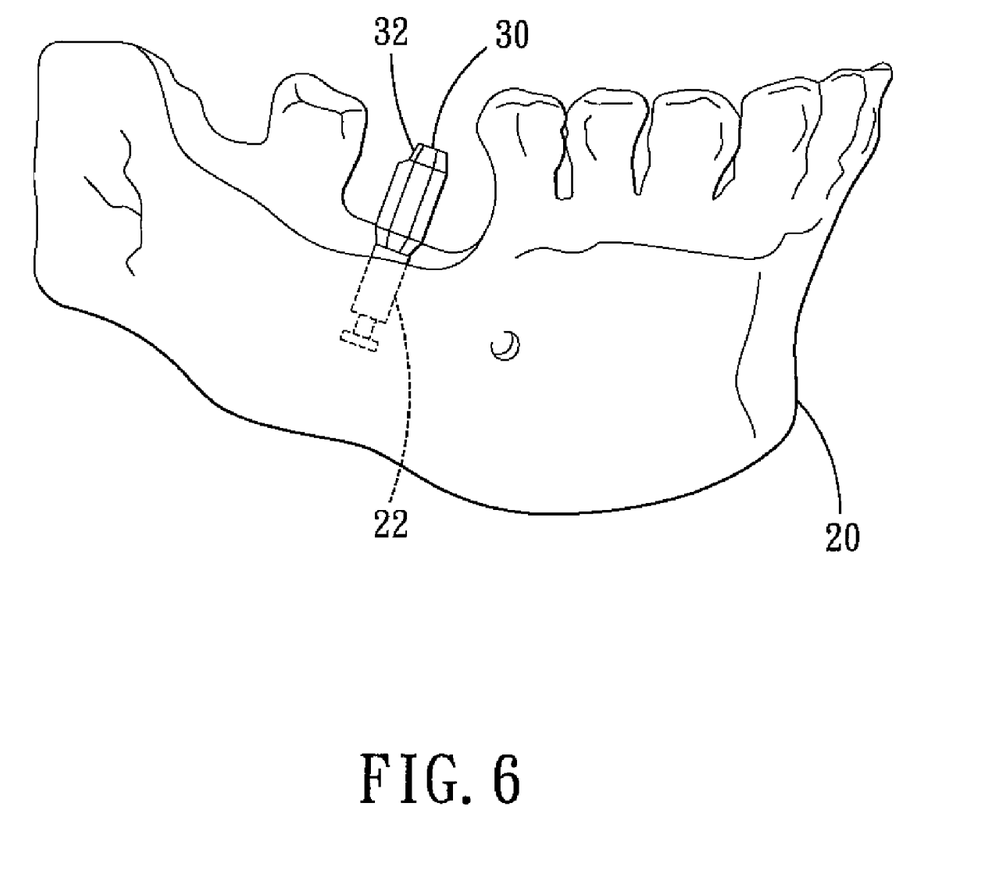
FIG. 6 is a schematic view of the step of setting the reference abutment device in accordance with the present invention, illustrating the state after the reference abutment device is set.
Figure 7:
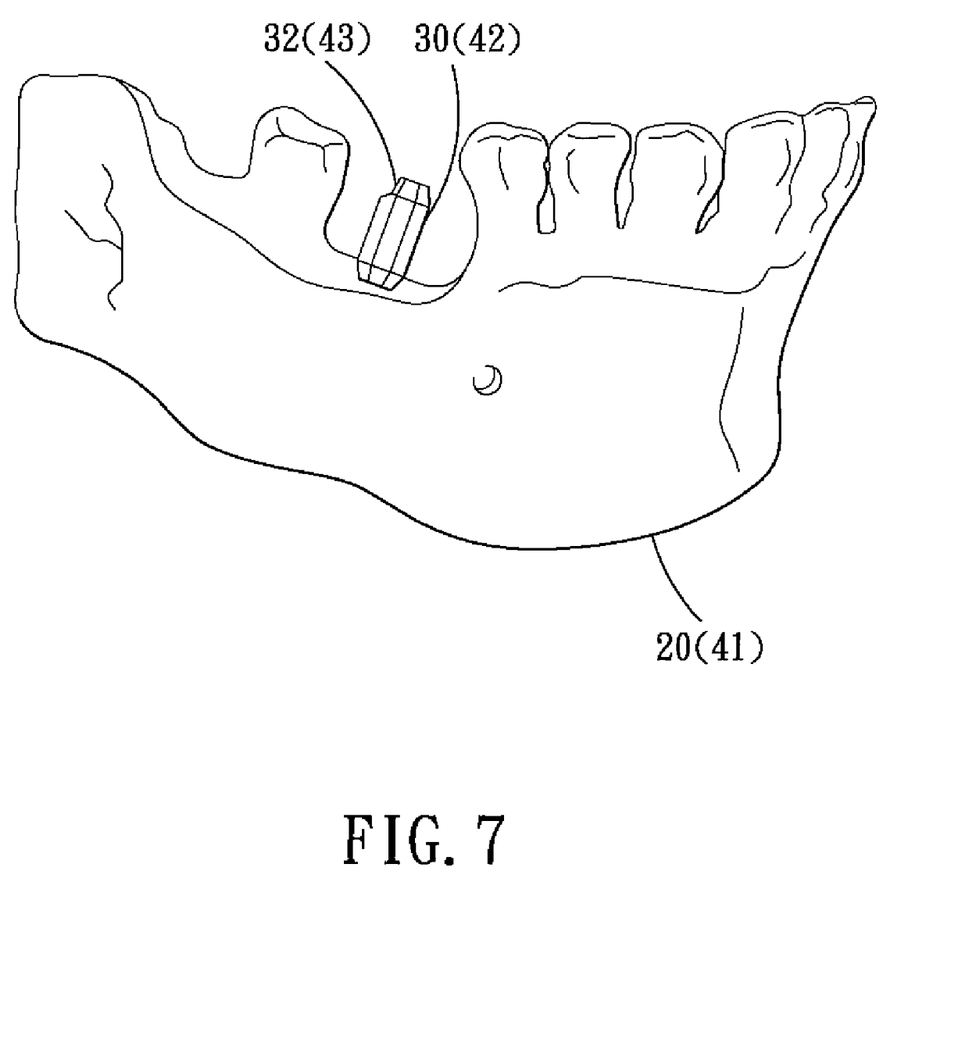
FIG. 7 is a schematic view of the step of scanning in accordance with the present invention, illustrating the scanned mouth model.
Figure 8:
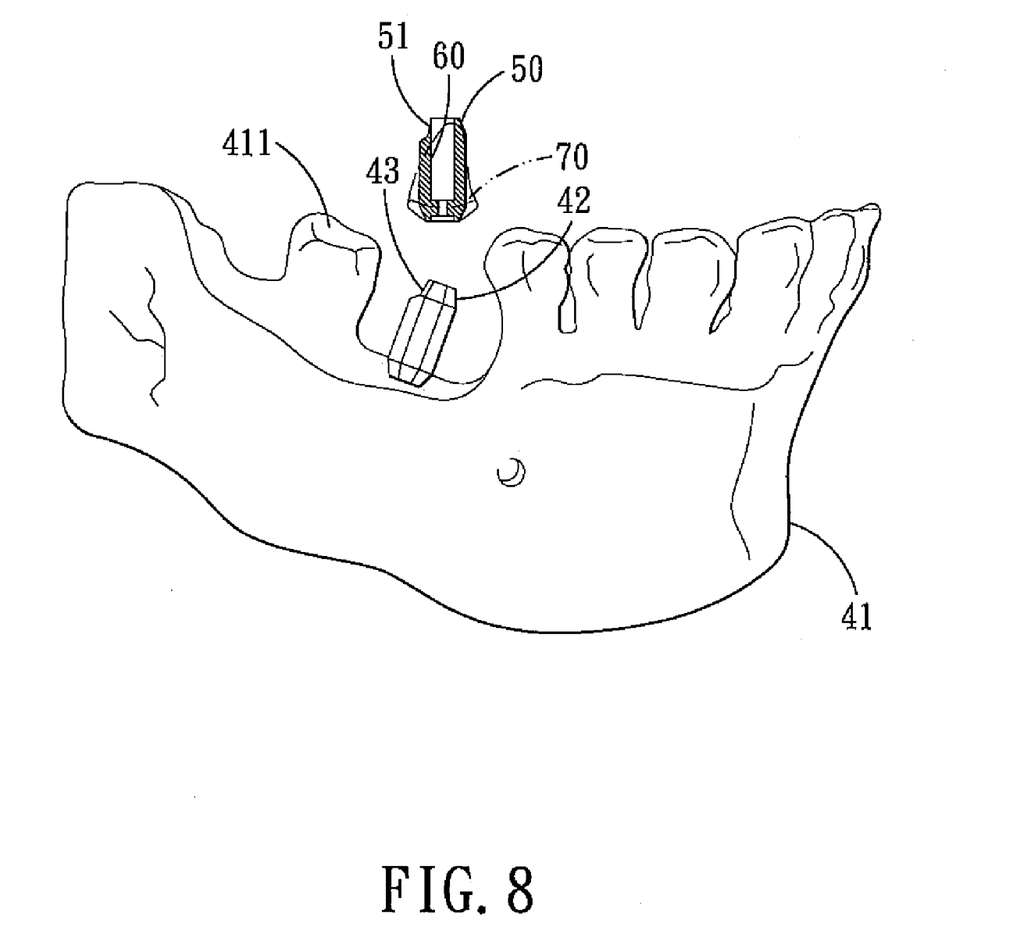
FIG. 8 is a first schematic view of the step of positioning, illustrating the state before the digital positioning abutment device, the interface, and the digital abutment are positioned.
Figure 9A:
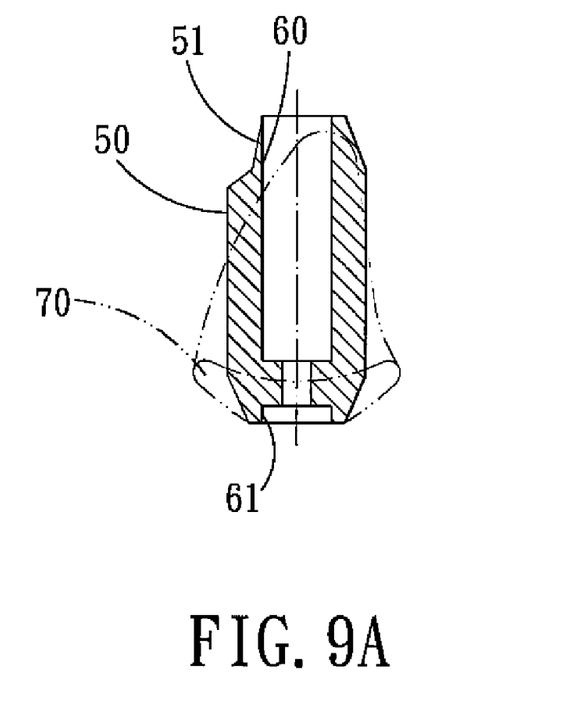
FIG. 9A is a side view of the digital positioning abutment device, the interface and the digital abutment, illustrating the configurations of the digital positioning abutment device, the interface, and the digital abutment.
Figure 9B:
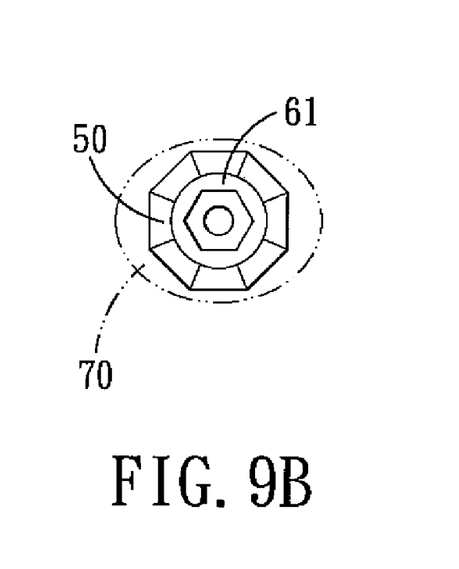
FIG. 9B is a bottom view of the digital positioning abutment device, the interface, and the digital abutment in accordance with the present invention, illustrating that the bottoms of the digital positioning abutment device, the interface, and the digital abutment are hexagonal.
Figure 10:
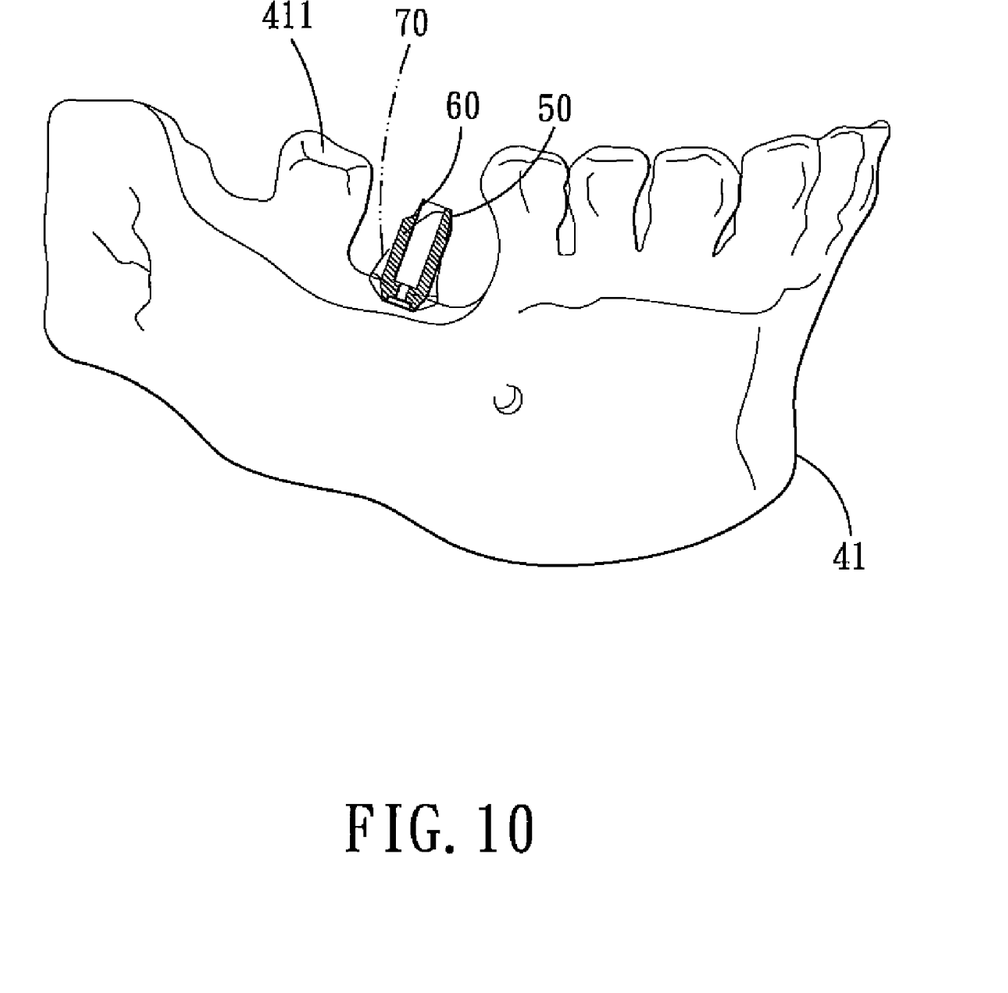
FIG. 10 is a second schematic view of the step of positioning, illustrating the state after the digital positioning abutment device, the interface, and the digital abutment are positioned.

As shown in FIGS. 4-5B, in the step of setting a reference abutment device, which consists of fetching a reference abutment device 30 configured correspondingly to the analog 22, the reference abutment device 30 includes an interface 31, and the outer surface of the reference abutment device 30 includes at least one feature 32. In the present embodiment, the interface 31 of the reference abutment device 30 is in the shape of a hexagon, but it can also be in the shapes corresponding to the interface of the analog, such as a triangle, petal shape, and so on. The feature 32 of the reference abutment device 30 may be a concave configuration. A locking member 33 is inserted into a through hole 34 of the reference abutment device 30 and locked into a threaded hole 222 of the analog 22 for connecting the reference abutment device 30 with the analog 22. The interface 31 of the reference abutment device 30 and the interface 221 of the analog 22 are connected, as shown in FIG. 6. After connection, the feature 32 of the reference abutment device 30 is not blocked, that is, the feature 32 is exposed toward the outside of the mouth model 20 and the analog 22 to be scanned to obtain the digital data. It is to be noted that, if the dental implant site of the oral cavity model is a posterior site, the reference abutment device 30 is set at the position of the posterior site of the mouth model 20, and the feature 32 is optimally set facing the buccal side. If the dental implant site of the oral cavity model is an anterior site, the reference abutment device 30 is set at the position of the anterior site of the oral cavity model 20, and the feature 32 is optimally set facing the labial side.

As shown in FIGS. 8-11A, in the step of positioning, which consists of taking a digital positioning abutment device 50 shaped the same as the reference abutment device 30, a positioning element 60 within the digital positioning abutment device 50, and a digital abutment 70 from a database, where the digital positioning abutment device 50 includes at least one feature 51, and the positioning element 60 includes an interface 61 on the bottom thereof. The interface 61 and the feature 51 of the digital positioning abutment device are shaped and positioned correspondingly to the interface 31 and the feature 32 of the reference abutment device 30, that is, both interfaces are hexagonal and both features are concave. The interface 61 of the positioning element 60 can also be in the shape of a triangle, a petal shape, and so on. The digital positioning abutment device 50 is superimposed on the digital reference abutment device 42 according to the features 43, 51 and substitutes for the digital reference abutment device 42, so as to obtain the digital configuration data after positioning the interface 61 of the positioning member 60 of the positioning abutment device 50 on the interface 221 of the analog 22. In addition, the digital abutment 70 is superimposed on the digital reference abutment device 42. By referring to the configuration of an adjacent tooth 411 of the digital mouth model 41, the digital abutment 70 can be superimposed on the digital reference abutment device 42 more exactly. It is to be noted that, the digital abutment 70 can also be superimposed on the digital reference abutment device 42 with the digital positioning abutment device 50.

Figure 11A:
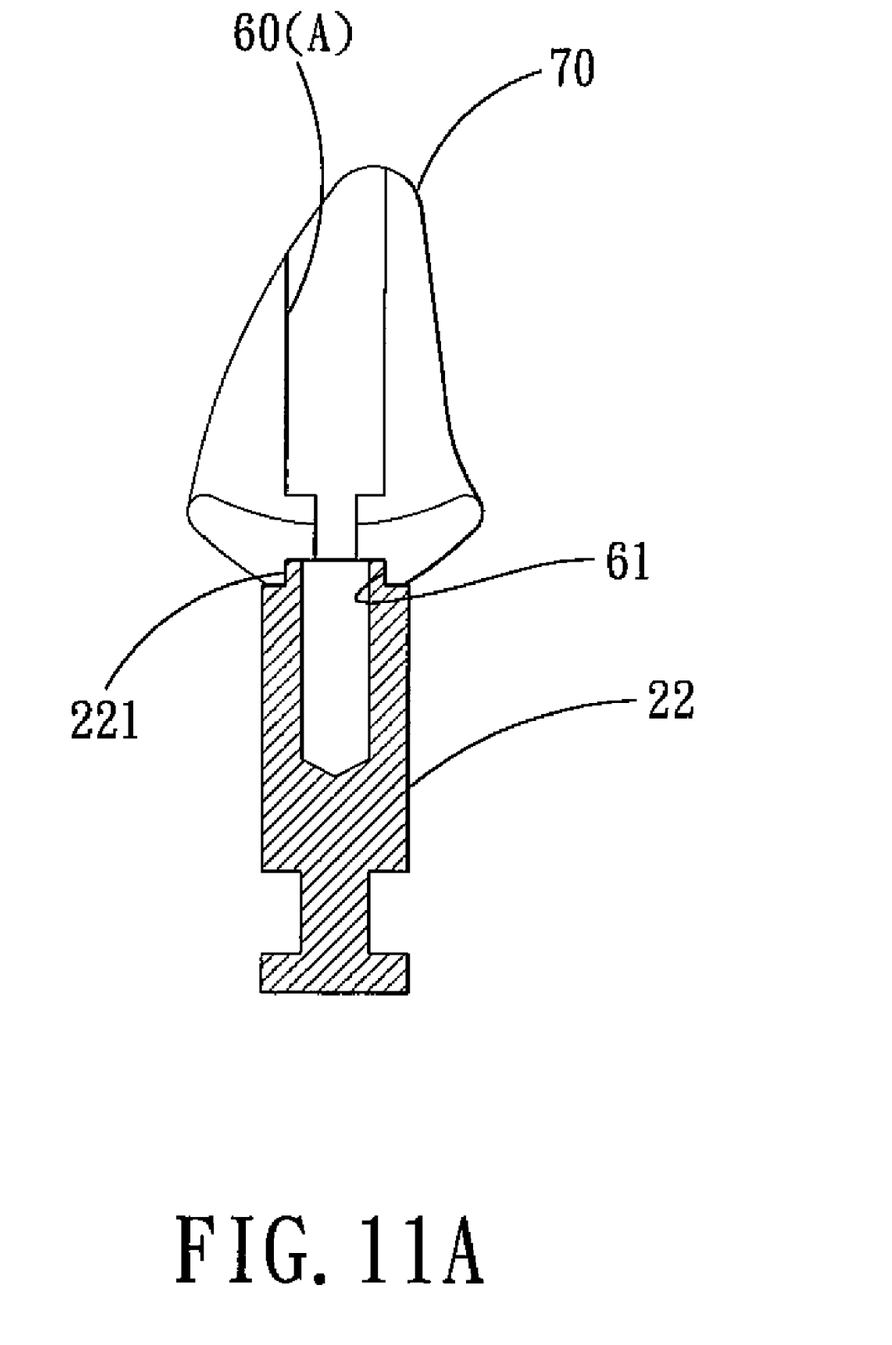
FIG. 11A is a first view of the step of adjusting in accordance with the present invention, illustrating the digital configuration data after the digital positioning abutment device and the analog are positioned.
Figure 11B:
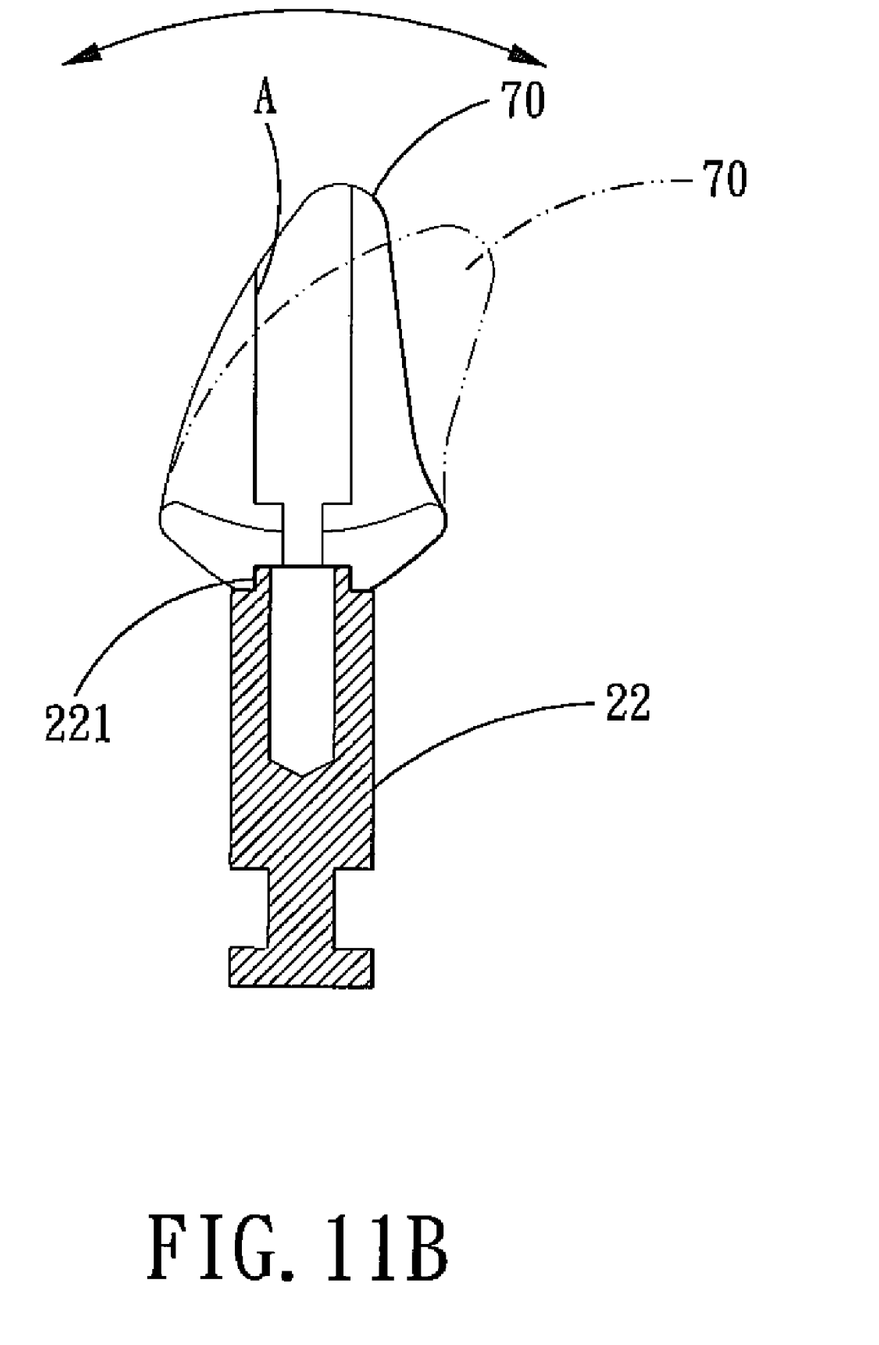
FIG. 11B is a second view of the step of adjusting in accordance with the present invention, illustrating the operation of adjusting the digital abutment.
Figure 12:
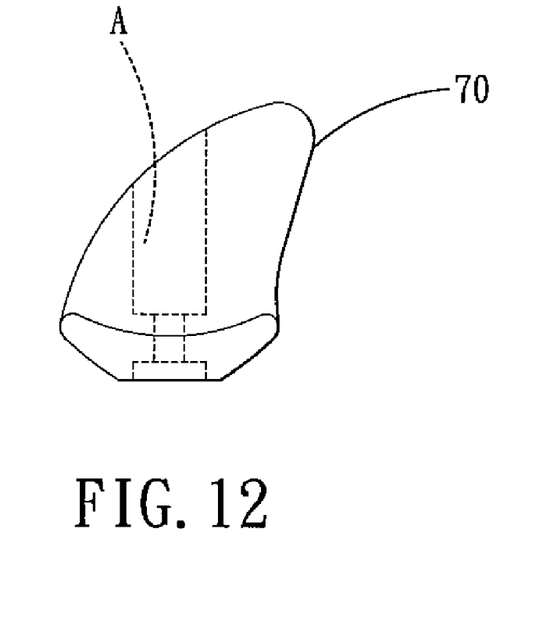
FIG. 12 is a schematics view of the abutment in accordance with the present invention, illustrating the adjusted digital abutment.
Figure 13:
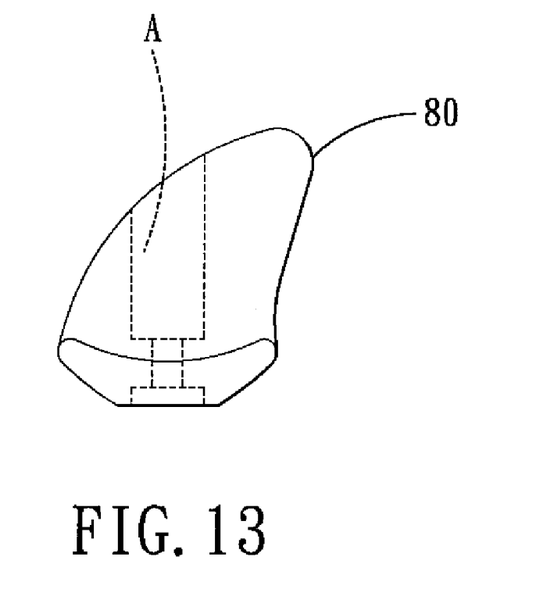
FIG. 13 is another schematic view of the abutment in accordance with the present invention, illustrating the abutment product fabricated after the digital abutment is adjusted.

As shown in FIGS. 11A-11B, in the step of adjusting, by obtaining both the digital configuration data of the digital positioning abutment device 50 and the analog 22, the digital abutment 70 can be optimally adjusted without affecting the connection configuration of the digital abutment 70 and the analog 22, thus finishing the design of the abutment, as shown in FIG. 12.

To summarize, with a reference abutment device 30 having a feature 32, the present invention obtains the configuration digital data A required for adjusting the digital abutment 70, such as angle, direction, and so on. Accordingly, please refer to FIGS. 11A-11B. Based on the digital configuration data A after positioning the interfaces 61, 221 of the positioning member 60 on the interface of the analog 22, the digital abutment 70 can be adjusted and rectified by referring to the configuration of the adjacent tooth 411 or other related information. During the adjusting and rectifying processes, the digital configuration data A does not change with the adjustment of the digital abutment 70. After the adjustment, the data of the digital abutment 70 is output to a fabricating system for fabrication of an abutment 80 product with the same configuration as the abutment 80.

Hence, the present invention can adjust the digital abutment 70 based on the requirements, and the adjusted digital abutment 70 has no influence on the configuration relationship with respect to the analog 22, such as angle, direction, and so on. Accordingly, when an abutment 80 product which is fabricated according to the adjusted abutment 80 is installed at the dental implant site in the patient's mouth, there is no configuration deviation between the abutment 80 product and the implant because the configuration relationship between them is maintained, such that the occlusion functionality of the sequent artificial tooth and the esthetics of the artificial tooth after dental implantation are improved.

While we have shown and described various embodiments in accordance with the present invention, it is clear to those skilled in the art that further embodiments may be made without departing from the scope of the present invention.

What is claimed is:

1. A method for designing an abutment tooth comprising the steps of:

acquiring an oral cavity model: reproducing an internal shape of a patient's oral cavity to form an oral cavity model, the oral cavity model has a copy artificial tooth analog at a dental implant position thereof, the copy tooth analog includes an interface;

setting a reference fixture: fetching a reference fixture, the reference fixture includes an interface and includes at least one feature point which is a concave configuration on an outer surface thereof, the interface of the reference fixture is positioned on the interface of the copy tooth analog without shielding the feature point of the reference fixture;

scanning: scanning the oral cavity model to obtain a digital oral cavity model, a digital reference fixture and a digital feature point;

positioning: taking a digital positioning fixture, a positioning member combined with the positioning fixture and a digital abutment tooth from a database, wherein the digital positioning fixture includes at least one feature point according to which the digital positioning fixture is superposed on the digital reference fixture and substitutes the digital reference fixture, so as to obtain configuration digital data after mutual positioning of the interfaces of the positioning member of the digital positioning fixture and the copy tooth analog, the digital abutment tooth is superposed on the digital reference fixture;

adjusting: optimally adjusting the digital abutment tooth by obtaining configuration data of the digital positioning fixture and the copy tooth analog, thus finishing the design of the abutment tooth.

2. The method for designing an abutment tooth as claimed in claim 1, wherein if the dental implant position of the oral cavity model is at a posterior tooth in the step of acquiring the oral cavity model, the reference fixture is set at the posterior tooth of the oral cavity model with the feature point thereof facing a buccal surface.

3. The method for designing an abutment tooth as claimed in claim 1, wherein if the dental implant position of the oral cavity model is at an anterior tooth in the step of acquiring the oral cavity model, the reference fixture is set at the anterior tooth of the oral cavity model with the feature point thereof facing a labial surface.

4. The method for designing an abutment tooth as claimed in claim 1, the digital abutment tooth is superposed on the digital reference fixture together with the digital positioning fixture in the step of positioning.

* * * * *